(12) United States Patent
Yu et al.

(10) Patent No.: US 10,584,308 B2
(45) Date of Patent: Mar. 10, 2020

(54) HOMOGENIZED AND INTEGRATED DEVICE WITH COAXIAL LINE AND DOUBLE-HIGH PRESSURE CYLINDER

(71) Applicant: Guangzhou Juneng Nano&Bio Technology Co., Ltd, Guangzhou, Guangdong Province (CN)

(72) Inventors: XingWen Yu, Guangzhou (CN); Qian Yu, Guangzhou (CN)

(73) Assignee: Guangzhou Juneng Nano&Bio Technology Co., Ltd, Guangzhou, Guangdong (CN)

(*) Notice: Subject to any disclaimer, the term of this patent is extended or adjusted under 35 U.S.C. 154(b) by 474 days.

(21) Appl. No.: 15/318,674

(22) PCT Filed: Mar. 31, 2015

(86) PCT No.: PCT/CN2015/075448
§ 371 (c)(1),
(2) Date: Dec. 14, 2016

(87) PCT Pub. No.: WO2016/037483
PCT Pub. Date: Mar. 17, 2016

(65) Prior Publication Data
US 2017/0130185 A1 May 11, 2017

(30) Foreign Application Priority Data

Sep. 11, 2014 (CN) .......................... 2014 1 0460631

(51) Int. Cl.
*C12M 1/02* (2006.01)
*B02C 19/18* (2006.01)
(Continued)

(52) U.S. Cl.
CPC .............. *C12M 27/00* (2013.01); *B02C 19/00* (2013.01); *B02C 19/18* (2013.01); *C12M 1/33* (2013.01);
(Continued)

(58) Field of Classification Search
CPC ........ C12M 27/00; C12M 1/33; C12M 29/14; C12M 45/02; C12M 47/06; C12M 47/08
See application file for complete search history.

(56) References Cited

U.S. PATENT DOCUMENTS

| 7,658,341 B2 * | 2/2010 | Rigaut .................... C12M 43/02 241/39 |
| 9,994,840 B2 * | 6/2018 | Dyer ..................... C12N 15/101 |

(Continued)

FOREIGN PATENT DOCUMENTS

| CN | 1724133 | 1/2006 |
| CN | 101624566 | 1/2010 |

(Continued)

OTHER PUBLICATIONS

"International Search Report (Form PCT/ISA/210) of PCT/CN2015/075448", dated Jul. 2, 2015, with English translation thereof, pp. 1-5.

*Primary Examiner* — Omar Flores Sanchez
(74) *Attorney, Agent, or Firm* — JCIPRNET

(57) ABSTRACT

A homogenized and integrated device with a coaxial line and double-high pressure cylinder, includes a long oil cylinder, two main connecting sleeves, two high pressure cylindrical homogenized main bodies, two auxiliary connecting sleeves and two short oil cylinders. The two main connecting sleeves, two high pressure cylindrical homogenized main bodies, two auxiliary connecting sleeves and two short oil cylinders are respectively and symmetrically arranged at two ends of the long oil cylinder and are assembled with the long oil cylinder along a same axial line. Each high pressure
(Continued)

cylindrical homogenized main body is integrally connected with the long oil cylinder by virtue of one of the main connecting sleeves. Each high pressure cylindrical homogenized main body is integrally connected with the corresponding short oil cylinder by virtue of one of the auxiliary connecting sleeves.

7 Claims, 3 Drawing Sheets

(51) Int. Cl.
  *C12M 1/33*   (2006.01)
  *B02C 19/00*   (2006.01)
  *F04B 9/113*   (2006.01)
  *C12N 1/06*   (2006.01)
  *F04B 31/00*   (2006.01)
  *C12M 1/00*   (2006.01)

(52) U.S. Cl.
  CPC ............ *C12M 29/14* (2013.01); *C12M 45/02* (2013.01); *C12M 47/06* (2013.01); *C12M 47/08* (2013.01); *C12N 1/066* (2013.01); *F04B 9/113* (2013.01); *F04B 31/00* (2013.01); *B02C 2019/183* (2013.01)

(56) References Cited

U.S. PATENT DOCUMENTS

| | | | |
|---|---|---|---|
| 2008/0108137 A1* | 5/2008 | Rigaut | C12M 43/02 |
| | | | 435/383 |
| 2010/0151540 A1* | 6/2010 | Gordon | B01F 5/0644 |
| | | | 435/134 |
| 2015/0368634 A1* | 12/2015 | Dyer | C12N 15/101 |
| | | | 435/259 |
| 2019/0032652 A1* | 1/2019 | McCarthy | F04B 27/02 |

FOREIGN PATENT DOCUMENTS

| | | |
|---|---|---|
| CN | 201381310 | 1/2010 |
| CN | 104195038 | 12/2014 |
| CN | 104212710 | 12/2014 |
| CN | 204079978 | 1/2015 |
| CN | 204079979 | 1/2015 |

* cited by examiner

HOMOGENIZED AND INTEGRATED DEVICE WITH COAXIAL LINE AND DOUBLE-HIGH PRESSURE CYLINDER

CROSS-REFERENCE TO RELATED APPLICATION

This application is a 371 application of an international PCT application serial no. PCT/CN2015/075448, filed on Mar. 31, 2015, which claims priority to and the benefit of China Patent Application No. CN201410460631.1, filed on Sep. 11, 2014, the disclosure of which is incorporated herein by reference in its entirety.

BACKGROUND OF THE INVENTION

1. Field of the Invention

The present invention generally relates to a homogenized compression device for a cell disrupter, in particular, to a homogenized and integrated device with a coaxial line and double-high pressure cylinder.

2. Description of Related Art

A technology of cell disruption is referred to a technology of disrupting cell membranes and cell walls via an external force, so that a cell content comprising a target product composition is released. The technology is fundamental to purification of a non-secretion type biochemical material (product) synthesized in cells. Combining great improvements of DNA recombination technology and tissue culture technology, proteins used to be considered as being difficult to obtain can be massively produced nowadays. Various methods for cell disruption have been developed in order to adapt to cell wall disruption of different purposes and types. Methods of disruption can be categorized as two major categories into mechanical methods and non-mechanical methods. Equipment applied by the mechanical methods varies; an ultra high pressure cell disruption device is generally used, which has comprehensive applications for disruption, micro-dispersion, particle nanonization and emulsification processing of biological cells, medicines, food, milk, cosmetics, chemical engineering materials, nano-materials and so forth. Disadvantages of the generally used ultra high pressure cell disruption device are: (1) applying a main oil cylinder with a single axis, which resulted in high energy consumption; (2) a liquid outlet is disposed at a top portion of a homogenized compression device, which causes difficulty in discharging liquid, i.e., residuals are easily formed; (3) a pressure gauge of the homogenized compression device is directly connected with a high pressure cavity, which results in frequent pulse of the pressure gauge that causes failure; (4) releasing energy at high pressure is likely to raise temperature; (5) a high pressure homogenized valve is susceptible to wear. Thus, a novel compression homogenized device is necessary to be developed to address the afore-mentioned issues.

SUMMARY OF THE INVENTION

The present invention is aimed to provide a homogenized and integrated device with a coaxial line and double-high pressure cylinder, which has a compact structure, reduces the usage of parts, and is advantageous for miniaturization and energy saving.

For realizing the afore-mentioned aim, the present invention provides a homogenized and integrated device with a coaxial line and double-high pressure cylinder, including a long oil cylinder, two main connecting sleeves, two high pressure cylindrical homogenized main bodies, two auxiliary connecting sleeves and two short oil cylinders. The two main connecting sleeves, two high pressure cylindrical homogenized main bodies, two auxiliary connecting sleeves and two short oil cylinders are respectively and symmetrically arranged at two ends of the long oil cylinder and are assembled with the long oil cylinder along a same axial line. Each high pressure cylindrical homogenized main body is integrally connected with the long oil cylinder by virtue of one of the main connecting sleeves, and each high pressure cylindrical homogenized main body is integrally connected with the corresponding short oil cylinder by virtue of one of the auxiliary connecting sleeves. A piston rod is disposed in the long oil cylinder, wherein the piston rod is capable of alternately protruding from the two ends of the long oil cylinder. Two ends of the piston rod are respectively connected with a pressurizing plunger rod in a high pressure cavity of each high pressure cylindrical homogenized main body. A homogenized valve in an inner cavity of each high pressure cylindrical homogenized main body is connected with an ejector rod of one of the short oil cylinders.

Because the two main connecting sleeves, the two high pressure cylindrical homogenized main bodies, the two auxiliary connecting sleeves and the two short oil cylinders are arranged symmetrically at the two sides of the long oil cylinder and assembled with the long oil cylinder along the same axial line, a structure of the homogenized and integrated device with a coaxial line and double-high pressure cylinder is compact and in a small volume, so as to be advantageous for miniaturization. In addition, the long oil cylinder has the piston rod capable of protruding from the two ends of the long oil cylinder, so as to perform cell disruption by the high pressure cylindrical homogenized main bodies at the two ends of the long oil cylinder. Comparing to a conventional homogenized and integrated device with single axial high pressure cylinder, the homogenized and integrated device with a coaxial line and double-high pressure cylinder can greatly save electricity, and can save energy at least for 30% to 40%, so as to greatly reduce energy consumption.

As a further improvement of the present invention, a feeding inlet is disposed at a top portion of an end of a high pressure cavity of each high pressure cylindrical homogenized main body and connected with the high pressure cavity. A pressure gauge connection port is disposed at a left side of each high pressure cylindrical homogenized main body and connected with the high pressure cavity. A liquid outlet is disposed at a right side of each high pressure cylindrical homogenized main body and connected with a sample outlet cavity of each high pressure cylindrical homogenized main body, the liquid outlet is connected with a bottom portion of the sample outlet cavity, and connected downwardly and vertically with a stainless steel cooling coil. Comparing to the prior art, of which a liquid outlet is disposed at a top portion of a high pressure cylindrical homogenized main body, this structure renders a fluent liquid discharge with smaller resistance, such that residuals are not readily formed in the high pressure cylindrical homogenized main bodies.

As a further improvement of the present invention, an integrated feeding device is connected to each feeding inlet. Each integrated feeding device includes a second check valve and a stocker. An inlet of a valve base of the second check valve is connected with a bottom portion of the stocker, an outlet of a valve body of each second check valve is connected with the corresponding feeding inlet, and the valve body of the second check valve and the stocker form an integrated structure. This structure can facilitate sample inlet and gas exhaust, and can further compact the structure of the homogenized and integrated device with a coaxial line and double-high pressure cylinder. Therefore, it is advantageous for miniaturization, and can reduce sample consumption during disruption, and is convenient for operation.

As a further improvement of the present invention, a first check valve is disposed in each pressure gauge connection port. A portion of a valve body of each first check valve is located in the corresponding high pressure cylindrical homogenized main body of high pressure cylinder, and composes an integrated structure with the corresponding high pressure cylindrical homogenized main body. This structure can further compact the structure of the homogenized and integrated device with a coaxial line and double-high pressure cylinder, so as to be advantageous for miniaturization. In addition, it can prevent pulses of a high pressure gauge, so as to prevent damage of the high pressure gauge.

As a further improvement of the present invention, a main view/adjustment port is disposed at a top portion of each main connecting sleeve, a water circulation port is disposed at a bottom portion of each main connecting sleeve, an auxiliary view/adjustment port is disposed at a top portion of each auxiliary connecting sleeve, an auxiliary water circulation port is disposed at a bottom portion of each auxiliary connecting sleeve. This structure can be convenient for inspection, adjustment and cooling water circulation.

As a further improvement of the present invention, an axial line of each high pressure cylindrical homogenized main body perpendicularly intersects with axial lines of the corresponding first check valve and the corresponding second check valve. This structure is advantageous for the pressure gauge to accurately measure the pressure in the high pressure cylindrical homogenized main bodies, and is advantageous for miniaturization design. Moreover, it is further advantageous for the pressure gauge to accurately measure the pressure in the homogenized and integrated device with pressurization.

As a further improvement of the present invention, a valve spool and the valve base of each first check valve are in planar contact and sealed therebetween, and a valve spool and the valve base of each second check valve are in planar contact and sealed therebetween as well. This structure is convenient for processing, and the operation stability of the first check valve and the second check valve is great, and the lifetime of this structure is extended.

As a further improvement of the present invention, a main view/adjustment port is disposed at a top portion of the main connecting sleeve, a water circulation port is disposed at a bottom portion of the main connecting sleeve, an auxiliary view/adjustment port is disposed at a top portion of the auxiliary connecting sleeve, an auxiliary water circulation port is disposed at a bottom portion of the auxiliary connecting sleeve. This structure can be convenient for inspection, adjustment and cooling water circulation.

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
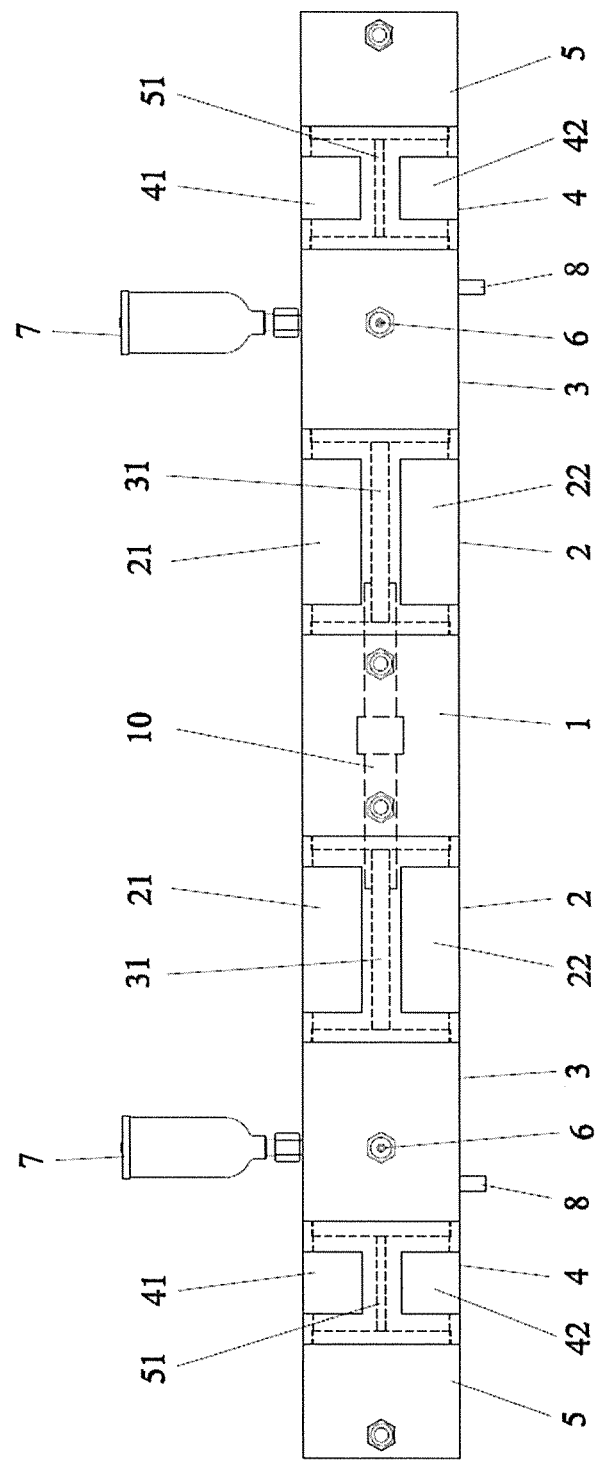
FIG. 1 is a front view of a homogenized and integrated device with a coaxial line and double-high pressure cylinder of the present invention.

Reference will now be made in detail to the present preferred embodiments of the invention, examples of which are illustrated in the accompanying drawings. Wherever possible, the same reference numbers are used in the drawings and the description to refer to the same or like parts.

Please refer to FIG. 1-4. A homogenized and integrated device with coaxial double-high pressure cylinder includes a long oil cylinder 1, two main connecting sleeves 2, two high pressure cylindrical homogenized main bodies 3, two auxiliary connecting sleeves 4 and two short oil cylinders 5. Two ends of the long oil cylinder 1 are connected to an end of a high pressure cylindrical homogenized main body 3 by virtue of a main connecting sleeve 2, another end of each high pressure cylindrical homogenized main body 3 is connected to a short oil cylinder 5 by virtue of an auxiliary connecting sleeve 4. The long oil cylinder 1, the main connecting sleeve 2, the high pressure cylindrical homogenized main body 3, the auxiliary connecting sleeve 4 and the short oil cylinder 5 are connected via a screw thread, and the long oil cylinder 1, the two main connecting sleeves 2, the two high pressure cylindrical homogenized main bodies 3, the two auxiliary connecting short sleeves 4 and the two oil cylinders 5 are assembled in a same axial line.

More specifically, a piston rod 10 is disposed in the long oil cylinder 1 that is capable of alternately protruding from the two ends of the long oil cylinder 1. An ejector rod 51 is disposed in the short oil cylinder 5 that is capable of protruding from an end of the short oil cylinder 5.

A main view/adjustment port 21 is disposed at a top portion of each main connecting sleeve 2. A water circulation port 22 is disposed at a bottom portion of each main connecting sleeve 2. An auxiliary view/adjustment port 41 is disposed at a top portion of each auxiliary connecting sleeve 4. An auxiliary water circulation port 42 is disposed at a bottom portion of each auxiliary connecting sleeve 4. The main view/adjustment port 21 and the auxiliary view/adjustment port 41 are disposed to facilitate viewing and adjusting. The water circulation port 22 and the auxiliary water circulation port 42 are disposed to facilitate cooling water circulation.

Figure 2:
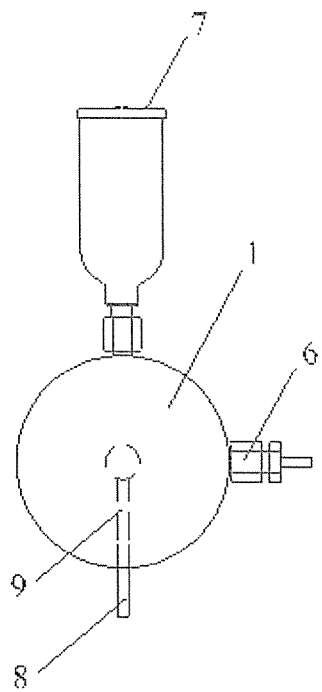
FIG. 2 is a left side view of the homogenized and integrated device with a coaxial line and double-high pressure cylinder of the present invention.
Figure 3:
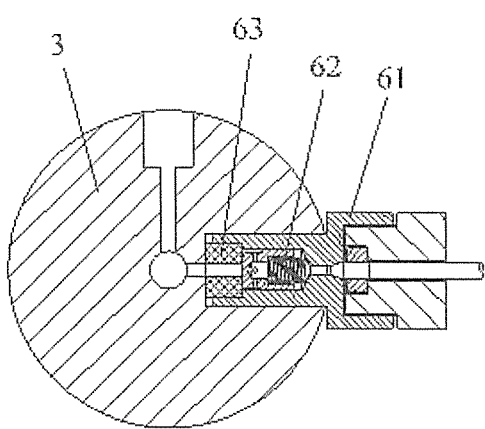
FIG. 3 is a cross-sectional view of a high pressure cylindrical homogenized main body and a first check valve.
Figure 4:
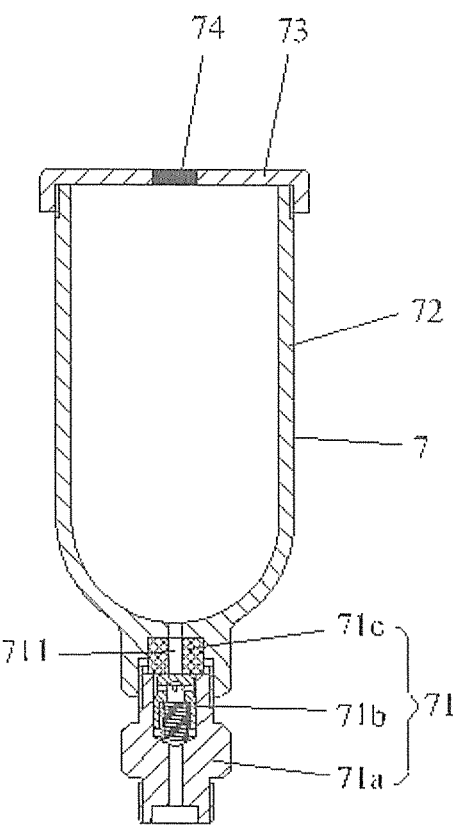
FIG. 4 is a cross-sectional view of an integrated feeding device.

A pressurizing plunger rod 31 capable of moving back and forth is disposed in each high pressure cylindrical homogenized main body 3. Each end of the piston rod 10 in the long oil cylinder 1 is connected with one pressurizing plunger rod 31 in a high pressure cavity of each high pressure cylindrical homogenized main body 3. A homogenized valve is further disposed in an inner cavity of each high pressure cylindrical homogenized main body 3 connected with the high pressure cavity. The homogenized valve in the inner cavity of each high pressure cylindrical homogenized main body 3 is connected to the ejector rod 51 of each short oil cylinder 5. In other words, dual directional oil cylinders are applied at two ends of each high pressure cylindrical homogenized main body 3, so as to greatly simplify a conventional integrated structure, reduce connecting components and check valves, and lower failure rate. Thus, it is facilitated for inspection and parts repair and renewal. The long oil cylinder 1 is a main oil cylinder at which the pressurizing plunger rods 31 move. The short oil cylinder 5 is an auxiliary cylinder controlling a disruption pressure. A pressure gauge connection port connected with the high pressure cavity is disposed at a left side of each high pressure cylindrical homogenized main body 3. A first check valve 6 is disposed in the pressure gauge connection port. A feeding inlet is disposed at a top portion of an end of the high pressure cavity of each high pressure cylindrical homogenized main body 3, an integrated feeding device 7 is connected to each feeding inlet, so that the integrated feeding device 7 is connected to the top portion of the end of the corresponding high pressure cavity, in order to facilitate sample inlet and gas exhaust. A liquid outlet 9 is further disposed at a right side of each high pressure cylindrical homogenized main body 3, the liquid outlet 9 is connected with a bottom portion of the sample outlet cavity, and is connected downwardly and vertically with a stainless steel cooling coil 8 (only a portion of the stainless steel cooling coil 8 is shown in FIG. 1 and FIG. 2). Thus, liquid discharging is fluent with lower resistance, residuals are not readily formed in the high pressure cylindrical homogenized main body.

It should be further noted that each first check valve 6 includes a first valve body 61, a first valve spool 62 and a first valve base 63. The first valve spool 62 and the first valve base 63 are located in a channel of the first valve body 61, and the first valve spool 62 and the first valve base 63 are in planar contact and sealed therebetween. Therefore, operation stability is improved, and lifetime is extended. A portion of each first valve body 61 is located in the corresponding high pressure cylindrical homogenized main body 3, and composes an integrated structure with each high pressure cylindrical homogenized main body 3. Another portion of each first valve body 61 is located outside of the high pressure cylindrical homogenized main body 3, so as to improve stability of the homogenized and integrated device with a coaxial line and double-high pressure cylinder, and prevent pulses of the high pressure gauge. Thus, the high pressure gauge is avoided from damage, and the homogenized and integrated device with a coaxial line and double-high pressure cylinder has a compact structure that is advantageous for miniaturization design.

Each integrated feeding device 7 includes a second check valve 71 and a stocker 72. An axial line of the high pressure cylindrical homogenized main body 3 and axial lines of the first check valve and the second check valve 71 are perpendicularly intersected. As a result, it is advantageous for the pressure gauge to accurately measure the pressure in the homogenized and integrated device with pressurization, and is advantageous for miniaturization design. Each second check valve 71 includes a second valve body 71*a*, a second valve spool 71*b* and a second valve base 71*c*. The second valve spool 71*b* and the second valve base 71*c* are located in a channel of the second valve body 71*a*, and the second valve spool 71*b* and the second valve base 71*c* are in planar contact and sealed therebetween. Thus, operation stability is improved, and lifetime is extended. The second valve body 71*a* and the stocker 72 form an integrated structure. An inlet 711 is disposed in the second valve base 71*c*, the inlet 711 and a bottom portion of the stocker 72 are connected directly. An outlet of the second valve body 71*a* is connected with the corresponding feeding inlet. Therefore, a long connection pipe is not required, so that consumption of a sample during disruption can be reduced greatly. In addition, a steel needle can be inserted to the stocker 72 to exhaust gas during gas exhaust of the second check valve 71, which is convenient and easy for operation. A cup cap 73 is disposed on the stocker 72. The cup cap 73 and the stocker 72 are connected by a sleeve manner or a screw thread manner, to facilitate adding samples and taking off the cup cap 73 during gas exhaust from the inside of the second check valve 71. A quick pipe coupler 74 is disposed on the cup cap 73 for cleaning rapidly, in order perform a cleaning operation on the stocker 72.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A homogenized and integrated device with a coaxial line and double-high pressure cylinder, comprising a long oil cylinder, two main connecting sleeves, two high pressure cylindrical homogenized main bodies, two auxiliary connecting sleeves and two short oil cylinders, wherein the two main connecting sleeves, two high pressure cylindrical homogenized main bodies, two auxiliary connecting sleeves and two short oil cylinders are respectively and symmetrically arranged at two ends of the long oil cylinder and are assembled with the long oil cylinder along a same axial line, each high pressure cylindrical homogenized main body is connected with the long oil cylinder by virtue of one of the main connecting sleeves; each high pressure cylindrical homogenized main body is connected with the corresponding short oil cylinder by virtue of one of the auxiliary connecting sleeves; a piston rod is disposed in the long oil cylinder, wherein the piston rod is capable of alternately protruding from the two ends of the long oil cylinder; two ends of the piston rod are respectively connected with a pressurizing plunger rod in a high pressure cavity of each high pressure cylindrical homogenized main body; a homogenized valve in an inner cavity of each high pressure cylindrical homogenized main body is connected with an ejector rod of one of the short oil cylinders.

2. The homogenized and integrated device with a coaxial line and double-high pressure cylinder according to claim 1, wherein a feeding inlet is disposed at a top portion of an end of a high pressure cavity of each high pressure cylindrical homogenized main body and connected with the high pressure cavity, a pressure gauge connection port is disposed at a left side of each high pressure cylindrical homogenized main body and connected with the high pressure cavity, a liquid outlet is disposed at a right side of each high pressure cylindrical homogenized main body and connected with a sample outlet cavity of each high pressure cylindrical homogenized main body, the liquid outlet is connected with a bottom portion of the sample outlet cavity, and connected downwardly and vertically with a stainless steel cooling coil.

3. The homogenized and integrated device with a coaxial line and double-high pressure cylinder according to claim 2, wherein an integrated feeding device is connected to each feeding inlet, each integrated feeding device comprises a second check valve and a stocker, an inlet of a valve base of the second check valve is connected with a bottom portion of the stocker, an outlet of a valve body of each second check valve is connected with the corresponding feeding inlet, and the valve body of the second check valve and the stocker form an integrated structure.

4. The homogenized and integrated device with a coaxial line and double-high pressure cylinder according to claim 3, wherein a first check valve is disposed in each pressure gauge connection port, a portion of a valve body of each first check valve is located in the corresponding high pressure cylindrical homogenized main body of high pressure cylinder, and composes an integrated structure with the corresponding high pressure cylindrical homogenized main body.

5. The homogenized and integrated device with a coaxial line and double-high pressure cylinder according to claim 4, wherein an axial line of each high pressure cylindrical homogenized main body perpendicularly intersects with axial lines of the corresponding first check valve and the corresponding second check valve.

6. The homogenized and integrated device with a coaxial line and double-high pressure cylinder according to claim 5, wherein a valve spool and the valve base of each first check valve are in planar contact and sealed therebetween, and a valve spool and the valve base of each second check valve are in planar contact and sealed therebetween as well.

7. The homogenized and integrated device with a coaxial line and double-high pressure cylinder according to claim 1, wherein a main view/adjustment port is disposed at a top portion of each main connecting sleeve, a water circulation port is disposed at a bottom portion of each main connecting sleeve, an auxiliary view/adjustment port is disposed at a top portion of each auxiliary connecting sleeve, an auxiliary water circulation port is disposed at a bottom portion of each auxiliary connecting sleeve.

* * * * *